United States Patent [19]

Parker et al.

[11] Patent Number: 4,980,371
[45] Date of Patent: Dec. 25, 1990

[54] ANTIRETROVIRAL FURAN KETONES

[75] Inventors: Roger A. Parker; Sai P. Sunkara, both of Cincinnati, Ohio

[73] Assignee: Merrell Dow Pharmaceuticals, Cincinnati, Ohio

[21] Appl. No.: 438,542

[22] Filed: Nov. 27, 1989

Related U.S. Application Data

[63] Continuation-in-part of Ser. No. 287,762, Dec. 21, 1988.

[51] Int. Cl.$^5$ ............................................. A61K 31/34
[52] U.S. Cl. .................................. 514/461; 514/473; 549/479; 549/488
[58] Field of Search ............... 549/488, 479; 514/461, 514/473

[56] References Cited

U.S. PATENT DOCUMENTS

| 2,746,973 | 5/1956 | Gregory | 549/479 |
| 4,000,164 | 12/1976 | Parker | 549/479 |
| 4,009,187 | 2/1977 | Eliasson | 549/488 |
| 4,011,334 | 3/1977 | Parker | 549/479 |
| 4,110,351 | 8/1978 | Parker | 549/479 |
| 4,171,371 | 10/1979 | Diana | 514/461 |
| 4,288,443 | 8/1981 | Judd | 548/547 |
| 4,335,098 | 6/1982 | Parker | 514/461 |
| 4,382,814 | 5/1983 | Steffens | 549/479 |
| 4,602,099 | 7/1986 | Parker | 549/479 |
| 4,738,984 | 4/1988 | Parker | 514/461 |
| 4,791,133 | 12/1983 | Djoric et al. | 514/428 |
| 4,812,585 | 3/1989 | Konda | 549/488 |

FOREIGN PATENT DOCUMENTS 2518999 7/1983 France .
1539636 12/1977 United Kingdom .

OTHER PUBLICATIONS

G. D. Mayer et al., RMI 15,731, A New Antirhinovirus Compound, Intersci. Conf. Antimicrob. Agents Chemother, Atlanta, 1–4 Oct., 1978, (18th Conf.) (Abst 220).
R. J. Ash et al., RMI 15,731, An Inhibitor of Rhinovirus Replication, Intersci. Conf. Antimicrob. Agents Chemother., Atlanta, 1–4 Oct., 1978, (18th Conf.) (Abst 221).
Ash, Ronald J. et al., RMI 15,731 (1-[5-Tetradecyloxy-2-Furanyl]-Ethanone), A New Antirhinovirus Compound, Antimicrob. Agents Chemother, 16(3), 301–305 (1979).
Anon. RMI-15731, Drugs of the Future, 5, 306–307 (1980).
F. E. Hahn. Coming Drugs Against the Common Cold? Naturwissenschaften 66, 417–418 (1979).
Chemical Abstracts 102(23):197597d. Ninomiya, Y. et al., Comparative Studies on the Modes of Action of the Antirhinovirus Agents Ro 09–0410, Ro 09–0179, RMI--15,731, 4′,6-Dichloroflavan, and Enviroxime, Antimicrob. Agents Chemother., 27(4), 595–599 (1985).
Chemical Abstracts 106(1):197b. Ninomiya, Y. et al., Mechanism of Drug Resistance to Anti-Rhinovirus Agents Recent Adv. Chemother., Proc. Int. Congr. Chemother, 14th, Issue Antimicrobial Sect. 1, 379–380, Edited by: Ishigami, Joji Univ. Tokyo Press: Tokyo, Japan (1985).
Chemical Abstracts 106(13):95652h. Ishitsuka, H. et al., Molecular Basis of Drug Resistance to New Antirhinovirus Agents., J. Antimicrob. Chemother., 18(Suppl. B.), 11–18 (1986).
Parker, Roger A. et al., 5-(Tetradecyloxy-y)-2-Furan-Carboxylic Acid and Related Hypolipidemic Fatty Acid Like Alkloxyarylcarboxylic Acids, J. Med. Chem., 20(6), 781–791 (1977).

Primary Examiner—Donald G. Daus
Attorney, Agent, or Firm—Edlyn S. Simmons

[57] ABSTRACT

Furan ketone derivatives thereof having antiretrovirus activity and effective in a method of treatment of a retrovirus infection, have the formula

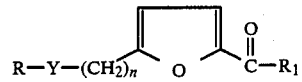

wherein Y is a bond, oxygen or divalent sulfur; n is 0 or 1; R is a straight or branched $C_{8-20}$ alkyl chain or a straight or branched $C_{8-20}$ alkenyl chain having from 1 to 4 double bonds; and $R_1$ is $C_{1-6}$ alkyl.

35 Claims, No Drawings

ANTIRETROVIRAL FURAN KETONES

This is a Continuation-in-Part of U.S. Ser. No. 287,762, filed Dec, 21, 1988, now abandoned.

FIELD OF INVENTION

The present invention relates to the use of certain substituted furan alkyl ketones in the treatment of retroviral infections including HIV infections.

BACKGROUND OF THE INVENTION

A great deal of research is currently underway to develop treatments and cures for viral infections in humans and in animals. Notably the incidence of acquired immune deficiency syndrome (AIDS) and AIDS related complex (ARC) in humans is increasing at an alarming rate. The five year survival rate for those with AIDS is dispiriting and AIDS patients, whose immune systems have been seriously impaired by the infection, suffer from numerous opportunistic infections including Kaposi's sarcoma and Pneumocystis carninii pneumonia. No cure is known and current treatments are largely without adequate proof of efficacy and have numerous untoward side effects. Fear of the disease has resulted in social ostracism of and discrimination against those having or suspected of having the disease.

Retroviruses are a class of ribonucleic acid (RNA) viruses that replicate by using reverse transcriptase to form a strand of complementary DNA (cDNA) from which a double stranded, proviral DNA is produced. This proviral DNA is then randomly incorporated into the chromosomal DNA of the host cell. Further transcription and translation of the integrated viral genome DNA results in viral replication through the synthesis of virus specific RNA and proteins.

Many of the known retroviruses are oncogenic or tumor causing. Indeed the first two human retroviruses discovered, denoted human T-cell leukemia virus I and II or HTLV-I and II, were found to cause rare leukemias in humans after infection of T-lymphocytes. The third such human virus to be discovered, HTLV-III, now referred to as HIV, was found to cause cell death after infection of T-lymphocytes and has been identified as the causative agent of acquired immune deficiency syndrome (AIDS) and AIDS related complex (ARC).

Among the substances previously shown to have activity against HIV and other retroviruses are such diverse compounds as azidothymidine, castanospermine, and heparin.

The applicants have now discovered that certain substituted furan ketones, more specifically furan ketones substituted at the 5-position of the furan ring by long chain alkyl and alkenyl moieties bonded to the furan ring either directly, through an ether or thioether bridge, or through an oxymethyl or thiomethyl bridge, are useful in the treatment of various retroviral infections including in the treatment of AIDS and ARC resulting from infection by HIV or other retroviruses.

SUMMARY OF THE INVENTION

The anti-retrovirus compounds of this invention have the general Formula I

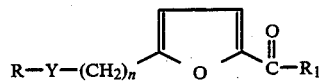

Formula I

In the above general Formula I, Y is a bond, O, or S; n is 0 or 1; R is a straight or branched $C_{8-20}$ alkyl chain or a straight or branched $C_{8-20}$ alkenyl chain having from 1 to 4 double bonds; and $R_1$ is $C_{1-6}$ alkyl.

DETAILED DESCRIPTION OF THE INVENTION

In the above general Formula I the substituent R may be a straight or branched saturated hydrocarbon chain having from 8 to 20 carbon atoms, in which case the R group may be represented as an alkyl chain of formula $C_qH_{2q+1}$ wherein q is an integer of from 8 to 20; or R is a straight or branched unsaturated hydrocarbon chain having from 8 to 20 carbon atoms and from 1 to 4 double bonds, in which case the R group may be represented as $C_qH_{2(q-z)+1}$ wherein q is an integer of from 8 to 20, and z is an integer of from 1 to 4 corresponding to the number of double bonds in the chain.

Illustrative examples of straight or branched saturated hydrocarbon chains which R may represent are, for example, decyl, undecyl, dodecyl, tridecyl, tetradecyl, 3,7-dimethyloctyl, 2,4-diethylhexadecyl, 3-methyloctadecyl, 1,7,10-trimethylundecyl, pentadecyl, hexadecyl, eicosyl, heptadecyl, 3-propylnonyl and octyl.

Illustrative examples of straight or branched unsaturated hydrocarbon chains containing from 1 to 4 double bonds which R may represent are, for example, 10-undecenyl; 9,12-octadecadienyl; 3,7,11-trimethyl-2,6,10-pentadecatrienyl; 3,7-dimethyl-2,6-octadienyl; 5,9-dimethyl-2,4,8-decatrienyl; 4,6-dimethyloct-3-enyl; 1,2,5,9-tetramethyl-2,4,8-decatrienyl; 1-ethenyl=2,4,6-decatrienyl and 2-hexadecenyl.

Illustrative examples of straight or branched lower alkyl groups of from 1 to 6 carbon atoms which $R_1$ may represent are methyl, ethyl, n-propyl, isopropyl, n-butyl, tert-butyl, neopentyl, and n-hexyl.

The novel furfuryl ethers and thioethers of general Formula II

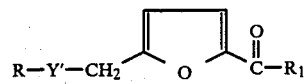

Formula II wherein Y' represents oxygen or divalent sulfur represent a preferred embodiment of this invention. Of the compounds of general Formula II, those wherein Y' is divalent sulfur are more preferred. Also, the compounds of general Formula II wherein $R_1$ is a straight chain alkyl are preferred over the branched chain alkyl derivatives. Compounds wherein $R_1$ is methyl are particularly preferred. Compounds wherein R is branched are preferred over compounds wherein R is a straight chain hydrocarbon are preferred. Compounds wherein R is unsaturated are preferred over compounds wherein R is saturated, with compounds wherein R has a single double bond being most preferred. Also, the compounds wherein R has from 13 to 18 carbon atoms are preferred. Another preferred embodiment of this invention is a pharmaceutical composition for the treatment of retrovirus infection comprising a compound of Formula II and a pharmaceutically acceptable carrier.

Another preferred embodiment of this invention is the use of compounds of general Formula I as antiretrovirus agents. The use of compounds of general Formula I wherein $R_1$ is a straight chain alkyl group are preferred, with $R_1$ as methyl being more preferred. Another preferred embodiment is the use of compounds of general Formula I as antiretrovirus agents wherein R has from 13 to 18 carbon atoms. The use of compounds of general Formula I wherein Y is oxygen or sulfur and n is 1 is another preferred embodiment, with Y as sulfur being more preferred. The use of compounds of general Formula I as antiretrovirus agents wherein R represents an unsaturated hydrocarbon chain having from 1 to 4 double bonds is preferred over the use of compounds wherein R represents a saturated hydrocarbon, with compounds having one double bond being most preferred. The use of compounds of general Formula I as antiretrovirus agents wherein R represents a branched hydrocarbon chain is preferred over the use of compounds wherein R represents a straight chain hydrocarbon.

The compounds of general Formula I wherein $R_1$ is methyl, Y is divalent sulfur or oxygen, n is 0 and R is a straight or branched saturated hydrocarbon chain having from 10 to 20 carbon atoms or a straight or branched unsaturated hydrocarbon chain having from 10 to 20 carbon atoms and from 1 to 4 double bonds are described as intermediates for the preparation of hypolipidemic agents in U.S. Pat. No. 4,032,647 and in U.S. Pat. No. 4,000,164.

The compounds of general Formula I wherein $R_1$ is $C_{1-4}$ alkyl, Y is a bond, divalent sulfur or oxygen, n is 0 and R is a straight or branched hydrocarbon chain having from 6 to 20 carbon atoms or a straight or branched unsaturated hydrocarbon chain having from 10 to 20 carbon atoms and from 1 to 4 double bonds or a straight or branched unsaturated hydrocarbon chain having from 6 to 9 carbon atoms and from 1 to 2 double bonds are described as antirhinovirus agents in Belgian patent No. 862,066.

Illustrative examples of compounds of general Formula I are the following:
methyl 5-(3,7,11-trimethyldodecyloxy)-2-furyl ketone
methyl 5-(9-octadecenyl)-oxy-2-furyl ketone
methyl 5-tetradecylthiomethyl-2-furyl ketone
methyl 5-(2-methyltetradecyloxy)-2-furyl ketone
methyl 5-tetradecyl-2-furyl ketone
methyl 5-tetradecyloxymethyl-2-furyl ketone
methyl 5-tetradecylthio-2-furyl ketone
methyl 5-decyloxy-2-furyl ketone
methyl 5-hexadecyloxy-2-furyl ketone
methyl 5-dodecyloxy-2-furyl ketone
methyl 5-dodecyl-2-furyl ketone
methyl 5-pentadecyloxy-2-furyl ketone
tert-butyl 5-tetradecyloxy-2-furyl ketone
hexyl 5-tetradecyloxy-2-furyl ketone
methyl 5-octadecyloxy-2-furyl ketone
ethyl 2-(5-dodecylthiomethylfuryl) ketone,
propyl 2-(5-decylthiofuryl) ketone,
isopropyl 2-(5-undecylthiofuryl) ketone,
butyl 2-(5-tridecylthiomethylfuryl) ketone,
tert-butyl 2-(5-octadecylthiofuryl) ketone,
propyl 2-(5-octylthiofuryl) ketone,
ethyl 2-(5-tridecyloxymethylfuryl) ketone,
ethyl 2-(5-dodecyloxyfuryl) ketone,
ethyl 5-tetradecyloxy-2-furyl ketone,
isopropyl 2-(5-octyloxymethylfuryl) ketone,
isopropyl 2-(5-hexadecylfuryl) ketone,
methyl 5-(3,7-dimethyloctyl)-2-furyl ketone,
methyl 5-(9,12-octadecadienyl)-2-furyl ketone, and
ethyl 5-(4,6-dimethyloct-3-enylthio)-2-furyl ketone.

The ability of the furan ketone derivatives of this invention to act as anti-retroviral agents can be demonstrated by their ability to inhibit the growth and replication of murine leukemia virus, an oncogenic retrovirus, as determined by an in vitro XC plaque assay. This assay was performed according to the method of Rowe et al. (*Viroloqy*, 1970, 42, 1136–39) as previously described by L. Hsu, et al. (*J. Virolooical Methods*, 1980, 1, 167–77) and T. L. Bowlin and M. R. Proffitt (*J. Interferon Res.*, 1983, 3(1), 19–31). Mouse SC-1 cells (fibroblast) ($10^5$) were seeded into each well of 6-well cluster plates (Costar #3506) in 4 ml Minimum Essential Medium (MEM) with 10% Fetal Calf Serum (FCS). Following an 18 hour incubation period (37° C.), Moloney murine leukemia virus (MoLV) was applied at a predetermined titer to give optimal (i.e. countable) numbers of virus plaques. Compounds were added 2 hours prior to addition of the virus. Three days later the culture medium was removed, the SC-1 cell monolayers were exposed to UV irradiation (1800 ergs), and rat XC cells ($10^6$) were seeded into each well in 4 ml MEM. Following an additional 3 day incubation (37° C.), these cells were fixed with ethyl alcohol (95%) and stained with 0.3% crystal violet. Plaques were then counted under low magnification. The antiviral activities of various compounds of this invention are tabulated in Table I in terms of the $IC_{50}$, i,e, the concentration giving a 50% inhibition of virus plaque growth.

TABLE 1

INHIBITORY CONCENTRATION OF VARIOUS FURAN KETONE DERIVATIVES OF FORMULA I AGAINST MURINE LEUKEMIA VIRUS

| Compound | $RY(CH_2)_n$ | $R_1$ | $IC_{50}$ ($\mu$g/ml) |
|---|---|---|---|
| Methyl 5-(3,7,11-trimethyl-dodecyloxy)-2-furyl ketone | 3,7,11-Trimethyl-dodecyloxy | $CH_3$ | <1 |
| Methyl 5-(cis-9-octadecenyl)-oxy-2-furyl ketone | n-(9-Octadecenyl)oxy | $CH_3$ | <1 |
| Methyl 5-tetradecylthio-methyl-2-furyl ketone | n-Tetradecythiomethyl | $CH_3$ | 1 |
| Methyl 5-tetradecyloxy-2-furyl ketone | n-Tetradecyloxy | $CH_3$ | 4 |
| Methyl 5-(2-methyltetradecyl-oxy)-2-furyl ketone | 2-Methyltetradecyloxy | $CH_3$ | 1–5 |
| Methyl 5-tetradecyl-2-furyl ketone | n-Tetradecyl | $CH_3$ | 1–10 |
| Methyl 5-tetradecyloxy- | n-Tetradecyloxymethyl | $CH_3$ | 1–10 |

TABLE 1-continued
INHIBITORY CONCENTRATION OF VARIOUS FURAN KETONE DERIVATIVES OF FORMULA I AGAINST MURINE LEUKEMIA VIRUS

| Compound | RY(CH$_2$)$_n$ | R$_1$ | IC$_{50}$ (µg/ml) |
|---|---|---|---|
| methyl-2-furyl ketone | | | |
| Methyl 5-tetradecylthio-2-furyl ketone | n-Tetradecythio | CH$_3$ | 1-10 |
| Methyl 5-decyloxy-2-furyl ketone | n-Decyloxy | CH$_3$ | 1-10 |
| Methyl 5-dodecyloxy-2-furyl ketone | n-Dodecyloxy | CH$_3$ | 1-10 |
| Methyl 5-hexadecyloxy-2-furyl ketone | n-Hexadecyloxy | CH$_3$ | 1-10 |
| Methyl 5-dodecyl-2-furyl ketone | n-Dodecyl | CH$_3$ | 5-10 |
| Methyl 5-pentadecyloxy-2-furyl ketone | n-Pentadecyloxy | CH$_3$ | 5-10 |
| t-Butyl 5-tetradecyloxy-2-furyl ketone | n-Tetradecyloxy | t-C$_4$H$_9$ | 5-10 |
| Hexyl 5-tetradecyloxy-2-furyl ketone | n-Tetradecyloxy | n-C$_6$H$_{13}$ | 5-10 |
| Methyl 5-octadecyloxy-2-furyl ketone | n-Octadecyloxy | CH$_3$ | >10 |

To further confirm the antiretroviral activity of these compounds, methyl 5-tetradecyloxy-2-furyl ketone and methyl 5-tetradecylthiomethyl-2-furyl ketone were evaluated for activity against HIV. Following overnight pretreatment of T-cells (JM cells) with the HIV1GB8 strain of HIV-1, the test compounds were added to the cell cultures at concentrations of 15 and 30 µg/ml. After 4 days the the number of synctial cells in the cell culture and the amount of p24 antigen, also a measure of viral replication, were determined. The data are shown in Table 2.

TABLE 2
ANTI-HIV ACTIVITY OF FURAN KETONES

| TREATMENT | SYNCYTIAL COUNT | % INHIBITION | P24 ANTIGEN pg × 10$^3$/ml |
|---|---|---|---|
| Untreated | 29 | — | 801 |
| Methyl 5-tetradecylthiomethyl-2-furyl ketone, 30 µg/ml | 0 | 100 | N. D. |
| Methyl 5-tetradecylthiomethyl-2- | 3 | 90 | 152 |
| Methyl 5-tetradecyloxy-2-furyl ketone, 30 µg/ml | 0 | 100 | N. D. |
| Methyl 5-tetradecyloxy-2-furyl ketone, 15 µg/ml | 19 | 34 | 450 |

N. D. = Not determined

The furan ketone derivatives of this invention can be used to treat a number of diseases and conditions known to be caused by retroviruses including those diseases and conditions caused by murine leukemia virus, feline leukemia virus, avian sarcoma virus, human immunodeficiency virus (HIV), HTLV-I, and HTLV-II. Those experienced in this field are readily aware of the circumstances requiring anti-retroviral therapy. Applicants consider the use of the furan ketone derivatives of this invention to treat HIV infections in humans to be of most importance. The term "patient" used herein is taken to mean mammals such as primates, including humans, sheep, horses, cattle, pigs, dogs, cats, rats and mice, and birds.

The amount of the furan ketone derivative of formula I to be administered can vary widely according to the particular dosage unit employed, the period of treatment, the age and sex of the patient treated, the nature and extent of the disorder treated, and the particular furan ketone derivative selected. Moreover the furan ketone derivative can be used in conjunction with other agents known to be useful in the treatment of retroviral diseases and agents known to be useful to treat the symptoms of and complications associated with diseases and conditions caused by retroviruses. The anti-retrovirally effective amount of a furan ketone derivative of formula I to be administered will generally range from about 15 mg/kg to 500 mg/kg. A unit dosage may contain from 25 to 500 mg of the furan ketone derivative, and can be taken one or more times per day. The furan ketone derivative can be administered with a pharmaceutical carrier using conventional dosage unit forms either orally or parenterally.

The preferred route of administration is oral administration. For oral administration the furan ketone derivative can be formulated into solid or liquid preparations such as capsules, pills, tablets, troches, lozenges, melts, powders, solutions, suspensions or emulsions. The solid unit dosage forms can be capsules, which can be of the ordinary hard- or soft-shelled gelatin type containing, for example, surfactants, lubricants, and inert fillers such as lactose, sucrose, calcium phosphate and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration, such as potato starch, alginic acid, corn starch and guar gum, lubricants intended to improve the flow of tablet granulations and to prevent the adhesion of tablet material to the surfaces of the tablet dies and punches, for example, talc, stearic acid, or magnesium, calcium or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The furan ketone derivatives of this invention may also be administered parenterally, that is, subcutaneously, intravenously, intramuscularly or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol or hexadecyl alcohol, glycols such as propylene glycol or polyethylene glycol, glycerol ketals such as 2,2-dimethyl-1,3-dioxolane-4-methanol, ethers such as poly(ethylene glycol) 400, an oil, a fatty acid, a fatty acid ester or glyceride, or an acetylated fatty acid glyceride, with or without the addition of a pharmaceutically acceptable surfactant such as a soap or a detergent, a suspending agent such as pectin, carbomers, methylcellulose, hydroxypropylmethylcellulose or carboxymethylcellulose, or an emulsifying agent, and other pharmaceutical adjuvants. Illustrative of oils which can be used in the parenteral formulations of this invention are those of petroleum, animal, vegetable, and synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl β-aminopropionates and 2-alkylimidazoline quarternary ammonium salts, as well as mixtures. The parenteral compositions of this invention will typically contain from about 0.5 to about 25% by weight of the furan ketone derivative of formula 1 in solution. Preservatives and buffers may also be used advantageously. In order to minimize or eliminate irritation at the site of injection, such compositions may contain a non-ionic surfactant having a hydrophilelipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The ketone compounds of general Formula I may be prepared by treating one equivalent of the corresponding carboxylic acid derivatives with two equivalents of alkyllithium, wherein the alkyl group corresponds to the desired $R_1$ substituent, as generally described by Fieser and Fieser, *Reagents for Organic Synthesis*, J. Wiley and Sons, Inc., New York, p. 688 (1967). This reaction is suitably carried out in solvents such as ether, tetrahydrofuran, p-dioxane, dimethoxyethane or diethyleneglycol dimethylether at temperatures of from −10° C. to the reflux temperature of the solvent for from ½ hour to 10 hours.

The ketone compounds of general Formula I may also be prepared by the reaction of alkyl magnesium bromide wherein the alkyl group corresponds to the desired $R_1$ substituent and the imidazolide derivative of an appropriately 5—R—Y(CH$_2$)$_n$ substituted 2-furancarboxylic acid derivative wherein R, Y, and n have the meanings defined in general Formula I. This reaction is carried out in a solvent such as ether, tetrahydrofuran, dioxane, dimethoxyethane, or acetonitrile. The reaction mixture is initially cooled to −10° C., after which the temperature is elevated to from about 25° C. to the reflux temperature of the solvent, and the reaction time varies from about ½ hour to 10 hours. The imidazolide derivative is obtained by treating an appropriate 5—R—Y(CH$_2$)$_n$ substituted 2-furancarboxylic acid derivative with N,N′-carbonyldiimidazole or by treatment of the 5—R—Y(CH$_2$)$_n$ substituted 2-furancarboxylic acid chloride, obtained by treating the substituted carboxylic acid with thionyl chloride, with two equivalents of imidazole, as generally described by H.A. Staab, *Anqew. Chem. Internat. Edit.* 1, 351 (1962).

The compounds of general Formula I may also be prepared by a Friedel-Crafts acylation of an appropriately R—Y(CH$_2$)$_n$ substituted furan, wherein R, Y, and n have the meanings defined in general Formula I, with an acyl halide of the formula

wherein halo is halogen, preferably chlorine or bromine and $R_1$ has the meaning defined above.

This reaction is carried out in the presence of an acid catalyst, for example, boron trifluoride-etherate, stannic chloride, zinc chloride, hydriodic acid or orthophosphoric acid, and optionally in the presence of a solvent, for example, methylene chloride, nitromethane or benzene. Suitable temperatures for this reaction may vary from −20° C. to the reflux temperature of the solvent, and the reaction time varies from about ½ hour to 10 hours.

The R—O— and R—S— substituted furancarboxylic acid derivative used herein can be prepared by aromatic nucleophilic substitution as generally described in J. March, *Advanced Organic Chemistry: Reactions, Mechanisms and Structure*, McGraw-Hill, p. 500 (1968), as outlined below.

Structure 1

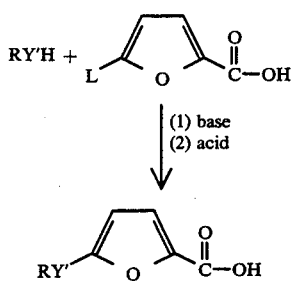

(1) base
(2) acid

Structure 2

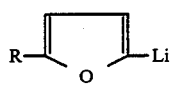

In the above general reaction, R has the meaning defined in general Formula I, Y' represents oxygen or divalent sulfur, and L represents a leaving group, such as nitro, fluoro, chloro, bromo or iodo, the preferred leaving group being chloro.

The above reaction may be carried out with or without a solvent. Suitable solvents for the reaction include benzene, xylene, toluene, chlorinated hydrocarbon solvents such as chlorobenzene, ethers such as bis(2-methoxyethyl) ether, 1,2-dimethoxyethane or anisole, hexamethylphosphoric triamide (HMPA), dimethylformamide, dimethylacetamide, 1-methyl-2-pyrrolidone, or pyridine. Preferred solvents are xylene, toluene and dimethylacetamide. Copper metal or a salt such as cuprous chloride may optionally be added to the reaction. Suitable bases for the reaction incude sodium or potassium metal, sodium hydride, potassium amide, potassium tert-butoxide or other strong bases such as potassium carbonate, potassium hydroxide, sodium hydroxide and sodium carbonate. The temperature of the reaction varies from about 25° C. to the reflux temperature of the solvent, and the reaction time varies from about 1 hour to about 7 days. Following completion of the reaction, the carboxylate salt derivative is treated with a mineral or organic acid to give compounds of structure 2.

Alcohols and mercaptans, as represented by RY'H, which find use in the above general reaction, are commercially available or may be prepared by reduction of the corresponding carboxylic acid or aldehyde.

The furoic acid derivatives represented by compounds of structure 1 may be prepared by several methods, as described in *The Furans*, by A.P. Dunlop and F.N. Peters, Reinhold Publishing Corp., pp. 80–169 (1953).

The R—Y— substituted furan carboxylic acid derivatives employed herein wherein Y is a bond can be prepared by treating a compound of the structure Structure 3

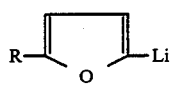

wherein R has the meaning defined in general Formula I with dry ice followed by the addition of water by procedures known in the art. The compounds of structure 3 are obtained by metalation of the appropriately R-substituted furan with butyllithium.

R—Y— substituted furan derivatives wherein Y is a bond can be obtained by the reaction of 2-lithiofuran, prepared by treating furan with butyllithium, with an R-halide, wherein R has the meaning defined in general Formula I by procedures generally known in the art. The R-halides used herein are generally commercially available or may be prepared by well-known procedures.

Likewise, the R—Y'-CH$_2$- substituted furan carboxylic acid derivatives used herein can be prepared by metalation followed by addition of carbon dioxide (carboxylation) as illustrated below.

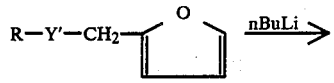

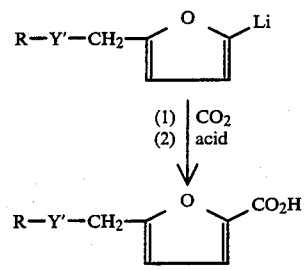

(1) CO$_2$
(2) acid

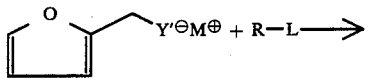

The RO—CH$_2$— and RS—CH$_2$— substituted furans can be obtained by reaction of furfuryl alcohol or furfuryl mercaptan by Williamson ether synthesis (J. March, "*Advanced Organic Chemistry- Reactions, Mechanisms and Structure,*" McGraw-Hill Book Company, New York, 1968, p. 316). The reaction is illustrated in the following reaction scheme:

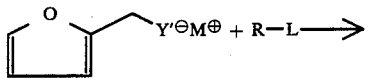

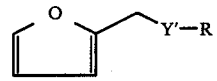

In the above reaction sequence, L represents a halogen atom, such as chlorine, bromine or iodine, or a sulfonate ester, such as methanesulfonate or p-toluenesulfonate; M+ represents a metal salt such as lithium, sodium, potassium, silver or mercury, and R and Y' have the meanings described above.

A furfuryl alkoxide salt, conveniently formed in situ by addition of a base such as sodium methoxide, potassium carbonate, sodium hydride or potassium hydroxide to the corresponding alcohol or mercaptan, is reacted with the desired R-hydrocarbon derivative bearing a leaving group on the terminal carbon atom. The leaving group is displaced, resulting in the formation of a carbon-oxygen or carbon-sulfur ether bond.

The L-substituted hydrocarbons used in the sequence are generally available commercially or by well-known, conventional synthetic methods.

The RY'—CH$_2$—substituted furan carboxylic acid derivative used herein may also be prepared from an ester of 5-methylfuran carboxylic acid by a Williamson ether synthesis as shown in the reaction scheme below:

An alkoxide salt, conveniently formed in situ by addition of a base such as sodium methoxide, potassium carbonate, sodium hydride or potassium hydroxide to the alcohol or mercaptan having the desired R hydrocarbon skeleton, is reacted with a 5-methylfuroic acid ester bearing a leaving group on the methyl carbon atom. The leaving group is displaced, resulting in the formation of a carbon-oxygen or carbon-sulfur ether bond, and the resulting 5—RY'(CH$_2$)—substituted 2-furoic acid ester is hydrolysed to the desired acid by methods well known in the art.

The alcohols, mercaptans and substituted furoic acid esters used in the sequence are generally available commercially or by well-known, conventional synthetic methods.

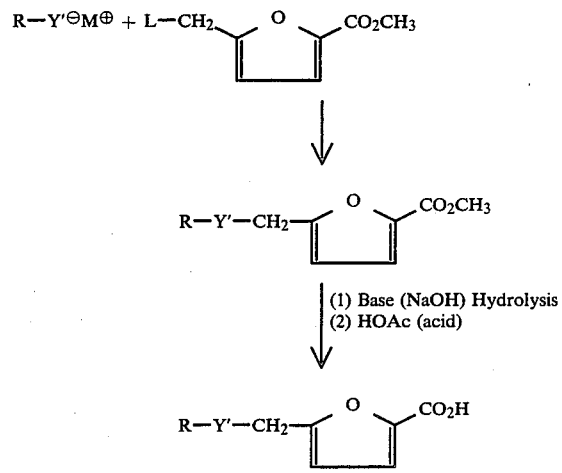

The Williamson reaction may be carried out with or without solvents. Suitable solvents for the reaction incude lower alcohols, such as ethanol and isopropanol, ketones such as acetone and butanone, or amides such as dimethylformamide and dimethylacetamide. Other suitable solvents include dimethylsulfoxide, acetonitrile, dimethoxyethane, tetrahydrofuran and toluene.

The temperature of the reaction may vary from about 0° C. to the reflux temperature of the solvent, and the reaction time may vary from about 0.5 hour to 80 hours.

The reaction is conveniently worked up by extraction of the product into an organic solvent such as ether, dichloromethane, chloroform, toluene or the like, washing with brine, drying over sodium or magnesium sulfate, and evaporation of the solvent. Purification is generally effected by distillation or crystallization from a suitable solvent.

The following specific examples synthesis of compounds useful in practicing the invention.

EXAMPLE 1

Methyl 5-tetradecyloxy-2-furyl ketone (A) A mixture of 125.0 g (0.652 mole) of 5-bromo-2-furoic acid, 210.0 g (0.978 mole) of 1-tetradecanol, 183.0 g (1.630 mole) of potassium tert-butoxide and 2500 ml of dimethyacetamide was heated with stirring. The tert-butanol formed in the reaction was allowed to distill off, then the mixture was heated to reflux with stirring for 48 hours. To the cooled mixture was added 6 liters of ice water, and the mixture was acidified with malonic acid. The resulting precipitate was collected, dried, and recrystallized twice from methanol to give 82.0 g (29%) of 5-tetradecycloxy-2-furoic acid, M.P. 112°-115° C. (dec.).

(B) A mixture of 82.0 g (0.235 mole) of 5-tetradecyloxy-2-furoic acid, 41.0 g (0.235 mole) of N,N'-carbonyldiimidazole and 800 ml tetrahydrofuran was stirred at room temperature during which time carbon dioxide gas was evolved. The reaction mixture was cooled to 0° C. to give N-[5-tetradecyloxy-2-furoyl]imidazole. The N- substituted imidazole, 50.0 g (0.134 mole) in 500 ml tetrahydrofuran was cooled in an ice bath. An equivalent amount of methyl magnesium bromide (50 ml of a 3 M solution in ether) was slowly added over a 2-hour period to the stirred mixture. The reaction was stirred for an additional 3 hours, then excess (500 ml) of 2N HCl was added and the product extracted into ether. The ether extract was separated, washed with water, dried over sodium sulfate, filtered, and evaporated to dryness to give methyl 5-tetradecyloxy-2-furyl ketone, M.P. 70°-72° C.

EXAMPLE 2

Butyl 5-(tetradecloxy)-2-furyl ketone

A mixture of 57.2 (0.300 mole) of 5-bromo-2-furoic acid, 102.0 g (0.45 mole) of tetradecanol, 18.0 g (0.750 mole) of sodium hydride and 2 liters of p-xylene are heated to reflux for 48 hours. The mixture is allowed to cool, then is acidified with acetic acid and diluted with 2 liters of water. The organic layer is separated, dried, evaporated to dryness, and the residue recrystallized from hexane to give 5-tetradecyloxy-2-furoic acid.

When in the procedure of Example 1(B) an appropriate amount of butyl magnesium bromide is substituted for methyl magnesium bromide, butyl 5-(tetradecloxy)-2-furyl ketone is obtained. M.P. 45°-8° C.

EXAMPLE 3

Methyl 5-(9,12,15-hexadecatrienyloxy) -2-furyl ketone

A mixture of 57.0 g (0.300 mole) of 5-bromo-2-furoic acid, 119.0 (0.450 mole) of 9,12,15-hexadecatrienol, and 84 g (0.750 mole) of potassium tert-butoxide in dry toluene is stirred with heating. The tert-butanol formed in the reaction is allowed to distill off, and the mixture is refluxed at 110° C. with stirring from 48 hours. The mixture is allowed to cool, then is acidified with acetic acid and diluted with ice water. The toluene organic layer is separated, washed with water, then extracted three times with 5% sodium bicarbonate solution. The combined aqueous extracts are cooled and acidified with 10% HCl solution to give 5-(9,12,15-hexadecatrienyloxy)-2-furoic acid.

When in the procedure of Example 1(B) an appropriate amount of 5-(9,12,15-hexadecatrienyloxy)-2-furoic acid is substutited for 5-tetradecyloxy-2-furoic acid, methyl 5-(9,12,15-hexadecatrienyloxy)-2-furyl ketone is obtained.

EXAMPLE 4

Methyl cis-5-(11-tetradecenyloxy)-2-furyl ketone (A) 8.8 g (0.0414 mole) of cis-11-tetradecen-1-ol was combined with 4.0 g (0.0829 mole) of sodium hydroxide (50% in oil) in 200 ml of dry toluene and heated to reflux with stirring for 3 hours. 6.1 g (0.414 mole) of 5-chloro-2furoic acid was added, followed by 25 ml of hexamethylphosphoric triamide (HMPA), and the reaction mixture refluxed with stirring for 20 hours, cooled, and acidified with acetic acid. The mixture was extracted into ether and the organic layer washed with water and with brine and evaporated to yield cis-5-(11-tetradecenyloxy)furan-2-carboxylic acid, M.P. 89°-90° C.

(B) A mixture of 4.2 g (0.013 mole) of cis-5-(11-tetradecenyloxy) furan-2-carboxylic acid and 50 ml of anhydrous ether was stirred at room temperature and 20.2 ml (0.0313 mole) of methyllithium (1.55 molar in hexane) added over 15 minutes. The mixture was stirred at room temperature for 3 hours and poured into saturated ammonium chloride solution. About 10 ml of glacial acetic acid was added and the phases separated. The ether layer was washed with water and evaporated to dryness to give a light yellow semisolid residue which was recrystallized twice from methanol to give methyl cis-5-(11-tetradecenyloxy)-2-furyl ketone, M.P. 36°–38° C.

EXAMPLE 5

Methyl 5-(2-methyletetradecyloxy)-2-furyl ketone (A) In the procedure of Example 4(A), 2-methyltetradecanol was substituted for cis-11-tetradecenol and 5-bromo-2-furoic acid substituted for 5-chloro-2-furoic acid to yield 5-(2-methyltetradecyloxy)-2-furancarboxylic acid, M.P. 88°–90° C.

(B) In the procedure of Example 4(B) 5-(2-methyltetradecyloxy)-2-furancarboxylic acid was substituted for cis-5-(11-tetradecenyloxy)-2-furancarboxylic acid to yield methyl 5-(2-methyltetradecyloxy)-2-furyl ketone, M.P. 45°–47° C.

EXAMPLE 6

Methyl 5-(3,7,11-trimethyldodecyloxy)-2-furyl ketone (A) In the procedure of Example 4(A), 3,7,11-trimethyldodecanol was substituted for cis-11-tetradecenol and 5-bromo-2-furoic acid substituted for 5-chloro-2-furoic acid to yield 5-(3,7,11-trimethyldodecyloxy)-2-furancarboxylic acid, M.P. 70°–73° C.

(B) In the procedure of Example 4(B), 5-(3,7,11-trimethyldodecyloxy)-2-furancarboxylic acid was substituted for cis-5-(11-tetradecenyloxy)furancarboxylic acid, to yield as a pale yellow oil, methyl 5-(3,7,11-trimethyldodecyloxy)-2-furyl ketone, B.P. 165° C. (0.25 mm Hg).

EXAMPLE 7

Methyl 5-pentadecyloxy-2-furyl ketone

In the procedure of Example 4, 1-pentadecanol was substituted for cis-11-tetradecen-1-ol to yield methyl 5-pentadecyloxy-2-furyl ketone, M.P. 67°–68° C.

EXAMPLE 8

Methyl 5-dodecyloxy-2-furyl ketone

In the procedure of Example 4, 1-dodecanol was substituted for cis-11-tetradecen-1-ol to yield methyl 5-dodecyloxy-2-furyl ketone, M.P. 66°–67° C.

EXAMPLE 9

Methyl 5-tridecyloxy-2-furyl ketone

In the procedure of Example 4, 1-tridecanol was substituted for cis-11-tetradecen-1-ol to yield methyl 5-tridecyloxy-2-furyl ketone, M.P. 61°–62° C.

EXAMPLE 10

Methyl 5-(cis-9-octadecen-1-yloxy)-2-furyl ketone

A mixture of 57.2 (0.300 mole) of 5-bromo-2-furoic acid, 121.0 g (0.45 mole) of cis-9-octadecenol, 18.0 g (0.750 mole) of sodium hydride and 2 liters of p-xylene are heated to reflux for 48 hours. The mixture is allowed to cool, then is acidified with acetic acid and diluted with 2 liters of water. The organic layer is separated, dried, evaporated to dryness, and the residue recrystallized from hexane to give 5-(cis-9-octadecen-1-yloxy)-2-furoic acid.

When in the procedure of Example 1(B) an appropriate amount of 5-(cis-9-octadecen-1-yloxy)-2-furoic acid is substituted for 5-(tetradecyloxy)-2-furoic acid, methyl 5-(cis-9-octadecen-1-yloxy)-2-furyl ketone is obtained.

EXAMPLE 11

Ethyl 5-(9,12,15-octadecatrien-1-yloxy)-2-furyl ketone

A mixture of 57.0 g (0.300 mole) of 5-bromo-2-furoic acid, 119.0 g (0.450 mole) of 9,12,15-octadecatrienol, and 84 g (0.750 mole) of potassium tert-butoxide in dry toluene is stirred with heating. The tert-butanol formed in the reaction is allowed to distill off, and the mixture is refluxed at 110° C. with stirring for 48 hours. The mixture is allowed to cool, then is acidified with acetic acid and diluted with ice-water. The toluene organic layer is separated, washed with water, then extracted three times with 5% sodium bicarbonate solution. The combined aqueous extracts are cooled and acidified with 10% HCl solution to give 5-(9,12,15-octadecatrien-1-yloxy)-2-furoic acid.

When in the procedure of Example 1 (B) an appropriate amount of 5-(9,12,15-octadecatrien-1-yloxy)-2-furoic acid is substituted for 5-(tetradecyloxy)-2-furoic acid, and an appropriate amount of ethyl magnesium bromide is substituted for methyl magnesium bromide, ethyl 5-(9,12,15-octadecatrien-1-yloxy)-2-furyl ketone is obtained.

EXAMPLE 12

Methyl 5-dodecyl-2-furyl ketone

A mixture of 68.1 g (1.0 mole) of furan and 500 ml of anhydrous ether is stirred at −20° C. after which 1.1 moles (458 ml of a 2.4 molar hexane solution) of butyllithium is added slowly with stirring. The reaction mixture is stirred for 1 hour, then 284 g (1.2 moles) of 1-bromododecane is added. The reaction mixture is stirred at room temperature for 4 hours after which it is poured into a saturated ammonium chloride solution. The organic layer is separated and washed with water and brine, dried over sodium sulfate and distilled under reduced pressure to give 2-dodecylfuran.

A solution of 30.4 g (0.2 moles) of 2-dodecylfuran in 300 ml of anhydrous ether is stirred at −20° C. after which 0.22 moles (92 ml of a 2.4 molar hexane solution) of butyllithium is added slowly with stirring. The reaction mixture is stirred for 1 hour then poured over 200 g of crushed dry ice (solid $CO_2$) after which the mixture is allowed to stand for 1 hour prior to dilution with a saturated ammonium chloride solution The organic layer is separated, washed with water and brine, dried over sodium sulfate and evaporated to give 5-dodecyl-2-furancarboxylic acid. The thus obtained acid in 500 ml of anhydrous ether is stirred at room temperature during which time 200 ml of a 2 molar solution of methyllithium in ether is added slowly. The reaction mixture is allowed to stand at room temperature for 2 hours after which it is poured into a saturated ammonium chloride solution The organic layer is separated and washed with water and brine, dried over sodium sulfate and evaporated to dryness to give white crystals of methyl 2-(5-dodecylfuryl) ketone. M.P. 35°–7° C.

EXAMPLE 13

Methyl 5-tetradecyloxymethyl-2-furyl ketone (A) A mixture of 9.8 g (0.1 mole) of furfuryl alcohol and 4.8 g (0.1 mole) of 50% sodium hydride in oil and 100 ml of dimethylformamide was stirred at room temperature for 1 hour 27.7 g (0.1 mole) of 1-bromotetradecane was added and the mixture stirred at room temperature overnight then heated to reflux for 1 hour. The mixture was cooled, diluted with water and extracted with diethylether. The ether was evaporated to dryness and distilled in a Kugelrohr under reduced pressure. 21.6 g of tetradecyl furfuryl ether as an oil was collected at 105°–140° C. (0.1 mmHg). (B) A mixture of 6.0 g (0.020 mole) tetradecyl furfuryl ether and 120 ml of diethylether was stirred in an ice-methanol bath (−10° C.) under positive argon. 17 ml (0.020 mole) of 1.2 molar n-butyllithium in hexane was added over 15 minutes and the mixture allowed to warm to room temperature for 1½ hours. The mixture was poured into a 1 liter flask containing dry ice and diethylether and allowed to warm to room temperature. The mixture was acidified with glacial acetic acid and water was added. The layers were separated and the ether layer was filtered and evaporated to dryness to give 6.3 g of a tan solid which was recrystallized from hexane-ether to give 1.5 g, tan solid 5-tetradecyloxymethyl-2-furancarboxylic acid, mp=86°–88° C.

(C) A mixture of 1.0 g (0.0029 mole) of 5-(tetradecyloxymethyl)-2-furancarboxylic acid and 50 ml of diethylether was cooled in an ice-methanol bath (−10° C.). Methyllithium (5.8 ml (0.007 mole) of 1.2 molar solution) was added over 15 minutes. The mixture was warmed to room temperature and stirred for 2 hours, then poured into saturated aqueous ammonium chloride solution and extracted. The ether layer was evaporated to dryness to give a white-yellow solid which was recrystallized from methanol to give 0.8 g light yellow solid methyl 5-tetradecyloxymethyl-2-furyl ketone, mp=61°–62° C.

EXAMPLE 14

Methyl 5-tetradecylthiomethyl-2-furyl ketone

In the procedure of Example 13, furfuryl mercaptan was substituted for furfuryl alcohol to yield methyl 5-tetradecylthiomethyl-2-furyl ketone, M.P. 55°–57° C.

EXAMPLE 15

| Solution | |
|---|---|
| Methyl 5-tetradecylthiomethyl-2-furyl ketone | 0.85 g |
| Alcohol | 78.9 ml |
| Isopropyl Myristate | 5.0 g |
| Polyethylene Glycol 400 (Av. M.W. 400) | 10.0 g |
| Purified Water sufficient to make | 100 ml |

Combine the alcohol, isopropyl myristate and polyethylene glycol 400 and dissolve the drug substance therein. Add sufficient purified water to give 100 ml.

EXAMPLE 16

| Tablets For 15,000 | |
|---|---|
| Methyl 5-(3,7,11-trimethyldodecyloxy)-2-furyl ketone | 75 g |
| Lactose | 1.216 kg |
| Corn Starch | 0.3 kg |

Compress on a suitable tablet machine to a weight of 0.115 g/tablet.

EXAMPLE 17

| Soft Gelatin Capsule | |
|---|---|
| Methyl 5-(cis-9-octadecen-1-yloxy)-2-furyl ketone | 0.25 kg |
| Polysorbate 80 (Polyoxyethylene (20) sorbitan mono-oleate) | 0.25 kg |
| Corn Oil sufficient to make | 25.0 kg |

Mix and fill into 50,000 soft gelatin capsules.

WHAT IS CLAIMED IS:

1. A method of treating a retroviral infection in a patient in need thereof which comprises administering to the patient an anti-retrovirally effective amount of a compound of the formula:

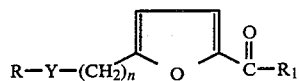

wherein Y is a bond, oxygen or divalent sulfur; n is 0 or 1; R is a straight or branched $C_{8-20}$ a alkyl chain or a straight or branched $C_{8-20}$ alkenyl chain having from 1 to 4 double bonds; and $R_1$ is $C_{1-6}$ alkyl.

2. A method according to claim 1 wherein n is 1.

3. A method according to claim 1 wherein n is 1 and Y is divalent sulfur.

4. A method according to claim 1 wherein R is a straight or branched $C_{13-18}$ alkyl chain or a straight or branched $C_{13-18}$ alkenyl Chain having from 1 to 4 double bonds.

5. A method according to claim 1 wherein R is a straight or branched $C_{8-20}$ alkenyl chain having from 1 to 4 double bonds.

6. A method according to claim 1 wherein R is a branched $C_{8-20}$ alkyl chain or a branched $C_{8-20}$ alkenyl chain having from 1 to 4 double bonds.

7. A method according to claim 1 wherein R is tetradecyl.

8. A method according to claim 1 wherein R is 9-octadecenyl.

9. A method according to claim 1 wherein R is 3,7,11-trimethyl-dodecyl.

10. A method according to claim 1 wherein R is 2-methyltetradecyl.

11. A method according to claim 1 wherein the compound is methyl 5-(3,7,11-trimethyl-dodecyloxy)-2-furyl ketone.

12. A method according to claim 1 wherein the compound is methyl 5-(9-octadecenyl)oxy-2-furyl ketone.

13. A method according to claim 1 wherein the compound is methyl 5-tetradecylthiomethyl-2-furyl ketone.

14. A method according to claim 1 wherein the compound is methyl 5-(2-methyltetradecyloxy)-2-furyl ketone.

15. A method according to claim 1 wherein the compound is methyl 5-tetradecyloxy-2-furyl ketone.

16. A compound of the formula

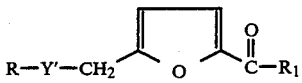

wherein Y' represents oxygen or divalent sulfur; R is a straight or branched $C_{8-20}$ alkyl chain or a straight or branched $C_{8-20}$ alkenyl chain having from 1 to 4 double bonds; and $R_1$ is $C_{1-6}$ alkyl.

17. A compound according to claim 16 wherein Y is divalent sulfur.

18. A compound according to claim 16 wherein R is a straight or branched $C_{13-18}$ alkyl chain Or a straight Or branched $C_{13-18}$ alkenyl chain having from 1 to 4 double bonds.

19. A compound according to claim 16 wherein R is a straight or branched $C_{8-20}$ alkenyl chain having from 1 to 4 double bonds.

20. A compound according to claim 16 wherein R is a branched $C_{8-20}$ alkyl chain or a branched $C_{8-20}$ alkenyl chain having from 1 to 4 double bonds.

21. A compound according to claim 16 wherein R is tetradecyl.

22. The compound according to claim 16 which is methyl 5-tetradecylthiomethyl-2-furyl ketone.

23. The compound according to claim 16 which is methyl 5-tetradecyloxymethyl-2-furyl ketone.

24. A pharmaceutical composition which comprises a compound of the formula

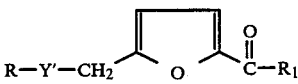

wherein Y' represents oxygen or divalent sulfur; R is a straight or branched $C_{8-20}$ alkyl chain or a straight or branched $C_{8-20}$ alkenyl chain having from 1 to 4 double bonds; and $R_1$ is $C_{1-6}$ alkyl; and a pharmaceutically acceptable carrier.

25. A pharmaceutical composition according to claim 24 wherein Y is divalent sulfur.

26. A pharmaceutical composition according to claim 24 wherein R is a straight or branched $C_{13-18}$ alkyl chain or a straight or branched $C_{13-18}$ alkenyl chain having from 1 to 4 double bonds.

27. A pharmaceutical composition according to claim 24 wherein R is tetradecyl.

28. A pharmaceutical composition according to claim 24 wherein the compound is methyl 5-tetradecylthiomethyl-2-furyl ketone.

29. A pharmaceutical composition according to claim 24 wherein the compound is methyl 5-tetradecyloxymethyl-2-furyl ketone.

30. A composition which comprises a compound of the formula

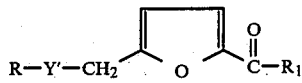

wherein Y' represents oxygen or divalent sulfur; R is a straight or branched $C_{8-20}$ alkyl chain or a straight or branched $C_{8-20}$ alkenyl chain having from 1 to 4 double bonds; and $R_1$ is $C_{1-6}$ alkyl; and an inert carrier.

31. A composition according to claim 30 wherein Y is divalent sulfur.

32. A composition according to claim 30 wherein R is a straight or branched $C_{13-18}$ alkyl Chain or a straight or branched $C_{13-18}$ alkenyl chain having from 1 to 4 double bonds.

33. A composition according to claim 20 wherein R is tetradecyl.

34. A composition according to claim 30 wherein the compound is methyl 5-tetradecylthiomethyl-2-furyl ketone.

35. A composition according to claim 30 wherein the compound is methyl 5-tetradecyloxymethyl-2-furyl ketone.

* * * * *

UNITED STATES PATENT AND TRADEMARK OFFICE
CERTIFICATE OF CORRECTION

PATENT NO. : 4,980,371
DATED : December 25, 1990
INVENTOR(S) : Roger A. Parker and Sai P. Sunkara It is certified that error appears in the above-identified patent and that said Letters Patent is hereby corrected as shown below:

Column 4, line 31 patent reads: "Virolooical" and should read --Virological--.

Column 4, line 64 patent reads: "_n-Tetradecyloxy" and should read --n-Tetradecyloxy--.

Column 5, line 31 patent reads: "days the the number" and should read --days the number--.

Column 5, line 43 patent reads: "Methyl 5-tetradecylthiomethyl-2-" and should read --Methyl 5-tetradecylthiomethyl-2-furyl ketone, 15 µg/ml--.

Column 5, line 49 patent reads "inventlon" and should read --invention--.

Column 7, line 10 patent reads "acceptably" and should read --acceptable--.

Column 12, line 58 patent reads "5-chloro-2furoic" and should read --5-chloro-2-furoic--.

Column 16, following line 5 insert: --Mix the active ingredient, the lactose and corn starch uniformly. Granulate with 10% starch paste. Dry to a moisture content of about 2.5%. Screen through a No. 12 mesh screen. Add and mix the following:

| | |
|---|---|
| Magnesium | 0.015 kg |
| Corn Starch sufficient to make | 1.725 kg-- |

UNITED STATES PATENT AND TRADEMARK OFFICE
CERTIFICATE OF CORRECTION

PATENT NO.   : 4,980,371
DATED        : December 25, 1990
INVENTOR(S)  : Roger A. Parker and Sai P. Sunkara It is certified that error appears in the above-identified patent and that said Letters Patent is hereby corrected as shown below:

Column 16, line 31, Claim 1 patent reads: "$C_{8-20}$ a alkyl" and should read --$C_{8-20}$ alkyl--.

Column 16, line 40, Claim 4 patent reads: "Chain" and should read --chain--.

Column 17, line 14, Claim 18 patent reads "Or a straight Or" and should read --or a straight or--.

Signed and Sealed this

Eleventh Day of August, 1992

Attest:

DOUGLAS B. COMER

*Attesting Officer*       *Acting Commissioner of Patents and Trademarks*